United States Patent [19]

DeSantis, Jr. et al.

[11] Patent Number: 5,604,244
[45] Date of Patent: Feb. 18, 1997

[54] INTRAOCULAR IRRIGATING SOLUTION CONTAINING A POLYAMINE ANTAGONIST

[75] Inventors: Louis DeSantis, Jr., Fort Worth; Michael A. Kapin, Arlington, both of Tex.

[73] Assignee: Alcon Laboratories, Inc., Fort Worth, Tex.

[21] Appl. No.: 486,841

[22] Filed: Jun. 7, 1995

[51] Int. Cl.$^6$ .................................................. A61K 31/445
[52] U.S. Cl. ........................................... 514/317; 514/912
[58] Field of Search .................................. 514/317, 912

[56] References Cited

U.S. PATENT DOCUMENTS 4,690,931  9/1987  Wick et al. ............................ 514/317

OTHER PUBLICATIONS

Beal, M. F., "Mechanisms of excitotoxicity in neurologic diseases," *FASEB J.*, 6:3338–3344 (1992).
Choi, D. W., "Excitotoxic cell death," *J. Neurobiol.*, 23:1261–1276 (1992).
Sattayasai, et al., "Morphology of quisqualate–induced neurotoxicity in the chicken retina," *Invest. Ophthalmol. Vis. Sci.*, 28: 106–117 (1987).
Tung et al., "A quantitative analysis of the effects of excitatory neurotoxins on retinal ganglion cells in the chick," *Visual Neurosci.*, 4:217–223 (1990).
Sisk et al., "Histological changes in the inner retina of albino rats following intravitreal injection of monosodium L–glutamate," *Graefe's Arch. Clin. Exp. Ophthalmol.*, 223:250–258 (1985).
Siliprandi et al., "N–methyl–D–aspartate–induced neurotoxicity in the adult rat retina," *Visual Neurosci.*, 8:567–573 (1992).
Reif–Lehrer et al., "Effects of monosodium glutamate on chick embryo retina in culture," *Invest. Ophthalmol. Vis. Sci.*, 14(2):114–124 (1975).
Blanks, J. C., "Effects of monosodium glutamate on the isolated retina of the chick embryo as a function of age: A morphological study," *Exp. Eye Res.*, 32:105–124 (1981).
Olney et al., "The role of specific ions in glutamate neurotoxicity," *Neurosci. Lett.*, 65:65–71 (1986).
Olney et al., "The anti–excitotoxic effects of certain anesthetics, analgesics and sedative–hypnotics," *Neurosci. Lett* 68:29–34 (1986).
Price et al., "CNQX potently and selectively blocks kainate excitotoxicity in the chick embryo retina," *Soc. Neurosci. Abst.*, 14:418 (1988).
David et al., "Involvement of excitatory neurotransmitters in the damage produced in chick embryo retinas by anoxia and extracellular high potassium," *Exp. Eye Res.*, 46:657–662 (1988).
Caprioli et al., "Large retinal ganglion cells are more susceptible to excitotoxic and hypoxic injury than small cells," *Invest. Ophthalmol. Vis. Sci.*, 34(Suppl):1429 (1993).
Cummins et al., "Electrophysiology of cultured retinal ganglion cells to investigate basic mechanics of damage," *Glaucoma Update IV*, 59–65 (1991).
Sucher et al., "N–methyl–D–aspartate antagonists prevent kainate neurotoxicity in rat retinal ganglion cells in vitro," *J. Neurosci.*, 11(4):966–971 (1991).
Massey, S., "Cell types using glutamate as a neurotransmitter in the vertebrate retina," N. N. Osborne and G. J. Chader (Eds.) *Progress in Retinal Research*, Ch. 9, Pergammon Press: Oxford, 399–425 (1990).
Miller et al., "Excitatory amino acid receptors in the vertebrate retina," in *Retinal Transmitters and Modulators: Models for the Brain*, (W. W. Morgan, Ed.) CRC Press, Inc., Boca Raton, II:123–160 (1985).
Zeevalk et al., "Action of the anti–ischemic agent infenprodil on N–methyl–D–aspartate and kainate–mediated excitotoxicity," *Brain Res.*, 522:135–139 (1990).
Ornstein et al., "Antagonists of the NMDA receptor complex," *DN&P*, 7(1):5–12 (1994).
Lipton, S. A., "Prospects of clinically tolerated NMDA antagonists: open–channel blockers and alternative redox states of nitric oxide," *TINS*, 16(12): 527–532 (1993).

*Primary Examiner*—Zohreh Fay
*Attorney, Agent, or Firm*—Sally Yeager

[57] ABSTRACT

Pharmaceutical compositions useful in ophthalmic surgery are described. The compositions include one or more polyamine antagonists, and are useful for preventing or treating excitotoxicity associated with ophthalmic surgery. Methods of using the compositions in connection with ophthalmic surgical procedures are also described.

10 Claims, No Drawings

INTRAOCULAR IRRIGATING SOLUTION CONTAINING A POLYAMINE ANTAGONIST

BACKGROUND OF INVENTION

1. Field of the Invention

The present invention relates to the field of ophthalmology. More particularly, the invention relates to an improved solution for maintaining the integrity, stability, and function of ocular tissues during invasive surgical procedures.

2. Discussion of Related Art

Vitreoretinal surgery, i.e., surgery involving the vitreous and retina of the posterior segment of the eye, has become commonplace as a result of the development of sophisticated surgical instrumentation and procedures. The retina is a very delicate tissue affected by a variety of diseases, such as diabetic retinopathy and cancer, as well as by physical trauma caused by accidental wounding of the eye. In an emergency vitreoretinal surgery case, the surgeon is sometimes challenged as the surgery proceeds and the extent of damage is revealed. As a result, such surgery may span a number of hours while the surgeon develops a strategy for repairing the retinal damage. This type of surgery calls for careful and deliberate decision-making and surgical precision to salvage as much viable retinal tissue, hence visual function, as possible. In any case, the surgeon wishes to avoid further damage due to the surgical procedure and manipulation of the tissue. Since the retina is exposed for some time to a potentially hostile environment as it lies open during the surgical procedure, some means for protecting retinal tissue is necessary.

When surgery of the anterior segment of the eye, usually cataract extraction with the implantation of an intraocular lens, is done, similar precautions against iatrogenic damage are routinely taken. Besides the use of careful surgical techniques, such precautions usually involve the use of a viscoelastic substance, such as sodium hyaluronate and/or chondroitin sulfate, to protect the corneal endothelium and the use of a physiological salt solution to rinse lens fragments from the eye. The anterior segment is bathed by the aqueous humor while the posterior segment contains the vitreous humor. The differences in the nature and composition of these two ocular humors relates to their respective functions and the tissues they subserve. For example, aqueous humor contains ascorbic acid which is secreted from the ciliary processes and has a consistency like that of water. On the other hand, vitreous humor has a viscous gel-like consistency. The avascular tissues of the anterior segment, i.e., the lens and cornea, depend upon the aqueous humor for nutrients and oxygen and for carrying away metabolic products. The retina receives its oxygen and nutrients from its copious vascular supply. In summary, the needs of the anterior and posterior segment tissues of the eye are similar in many respects but distinct in some.

Exdtotoxidty leads to neuronal injury due to excessive exdtatory amino acid ("EAA") stimulation. In the inner retina, glutamate is the major EAA that permits the bipolar and amacrine cells to communicate with the ganglion cell. In the central nervous system, exdtotoxidty results from hypoxia, ischemia, hypoglycemia or trauma. (See, for example, Baal, M. F., "Mechanisms of excitotoxicity in neurologic diseases," *FASEB J.*, 6:3338–3344 (1992); and Choi, D. W., "Excitotoxic cell death," *J. Neurobiol.*, 23:1261–1276 (1992).) Toxicity to the inner retina has been observed following intravitreal injection of EAAs following application of EAAs to the isolated animal retina or from exogenously applied glutamate to retinal ganglion cells in culture. See generally, Sattayasai, et al., "Morphology of quisqualate-induced neurotoxidty in the chicken retina," *Invest. Ophthalmol. Vis. Sci.*, 28:106–117 (1987); Tung et al., "A quantitative analysis of the effects of excitatory neurotoxins on retinal ganglion cells in the chick," *Visual Neurosci.*, 4:217–223 (1990); Sisk et al., "Histological changes in the inner retina of albino rats following intravitreal injection of monosodium L-glutamate," *Gracfe's Arch. Clin. Exp. Ophthalmol.*, 223:250–258 (1985); Siliprandi et al., "N-methyl-D-aspartate-induced neurotoxicity in the adult rat retina," *Visual Neurosci.*, 8:567–573 (1992); Reif-Lehrer et al., "Effects of monosodium glutamate on chick embryo retina in culture," *Invest. Ophthalmol. Vis. Sci.*, 14(2):114–124 (1975); Blanks, J. C., "Effects of monosodium glutamate on the isolated retina of the chick embryo as a function of age: A morphological study," *Exp. Eye Res.*, 32:105–124 (1981); Olney et al., "The role of specific ions in glutamate neurotoxidty," *Neurosi. Lett.*, 65:65–71 (1986); Olney et al., "The anti-excitotoxic effects of certain anesthetics, analgesics and sedative-hypnotics," *Neurosci. Lett* 68:29–34 (1986); Price et al., "CNQX potently and selectively blocks kainate excitotoxicity in the chick embryo retina," *Soc. Neurosci. Abst.*, 14:418 (1988); David et al., "Involvement of excitatory neurotransmitters in the damage produced in chick embryo retinas by anoxia and extracellular high potassium," *Exp. Eye Res.*, 46:657–662 (1988); Caprioli et al., "Large retinal ganglion cells are more susceptible to excitotoxic and hypoxic injury than small cells," *Invest. Ophthalmol. Vis. Sci,*, 34(Suppl):1429 (1993); Cummins et al., "Electrophysiology of cultured refinal ganglion cells to investigate basic mechanics of damage," *Glaucoma Update IV,* 59–65 (1991); and Sucher et al., "N-methyl-D-aspartate antagonists prevent kainate neurotoxidty in rat retinal ganglion cells in rat retinal ganglion cells in vitro," *J. Neurosci.*, 11(4):966–971 (1991).

EAA receptors have been characterized as metabotropic or ionotropic. Activation of a metabotropic receptor affects cellular processes via G-proteins; whereas ionotropic receptors affect the translocation of mono- and divalent cations across the cell membrane. There are at least three ionotropic receptors that have been named for the agonist that preferentially stimulates the receptor. These receptors have been classified as: N-methyl-D-aspartate (NMDA); kainate; and AMPA (2-amino-3-(3-hydroxy-5-methylisoxazol-4-yl) propanoic acid). These EAA receptors are differentially distributed to specific cells in the retina. (See, for example, Massey, S., "Cell types using glutamate as a neurotransmitter in the vertebrate retina," N. N. Osborne and G. J. Chader (Eds.) Progress in Retinal Research, Ch. 9, Pergammon Press: Oxford, 399–425 (1990); and Miller et al., "Excitatory amino acid receptors in the vertebrate retina," in *Retinal Transmitters and Modulators: Models for the Brain*, (W. W. Morgan, Ed.) CRC Press, Inc., Boca Raton, II:123–160 (1985).) The localization of such receptors would account for the pathologies associated with glaucoma or inner retinal ischemia. For example, death of the retinal ganglion cell has to a large part been attributed to the NMDA receptor. (See, for example, Sucher et al., "N-methyl-D-aspartate antagonists prevent kainate neurotoxicity in retinal ganglion cells in vitro," *J. Neurosci:*, 11(4):966–971 (1991).) Thus, antagonists of the NMDA receptor are neuroprotective; however, not all antagonists of the diversely distributed EAA receptors are neuroprotective to the inner retina through antagonism of the NMDA receptor, Zeevalk et al., "Action of the anti-ischemic agent ifenprodil on N-methyl-D-aspartate and kainate-mediated excitotoxicity," *Brain Res,* 522:135–139 (1990).

Glutamic acid is a neurotransmitter of the retina and is naturally found in that tissue. Certain cells within the retina have the ability to synthesize, release, take up and metabolize glutamic acid. It has been discovered that glutamic acid, in excessive quantity, is cytotoxic or neurotoxic to some retinal elements, notably retinal ganglion cells. Retinal ganglion cells are the cell bodies of origin for the optic nerve fibers which subserve vision. Glutamic acid is released from the retina during periods of ischemia and reperfusion, as may occur when the blood circulation is stopped and restarted in retinal blood vessels. Retinal ganglion cells, which lie close to the vitreous humor, are adversely affected by excessive glutamic acid. Glutamic acid is possibly released from retinal cells during vitreoretinal surgery if the tissue becomes anoxic or is physically traumatized. In this instance, glutamic acid could cause damage to retinal ganglion cells, and possibly other retinal cell types, unless it is prevented from interacting with its receptors located within those target cells. One means of prevention is to expose the retinal cells to an antagonist of glutamic acid during the vitreoretinal surgical procedure. Thus, bystander cells could be protected from the deleterious effects of glutamic acid and escape its toxicity. Since glutamic acid-producing cells are not known to exist in the anterior segment tissues of the eye, but are found in the retina, there is a higher probability for excessive glutamic acid damage to occur during vitreoretinal surgery compared to anterior segment surgery. This calls for the inclusion of an antagonist to glutamic acid in a physiological salt solution intended for use during vitreoretinal surgery. Even though such an antagonist may not be as useful for anterior segment surgery, it is unlikely that its presence would pose any hazard to those tissue. Thus, such a physiological salt solution could be used safely during anterior segment surgery too. The present invention is directed to satisfying the need for a physiological irrigating solution containing a glutamic acid antagonist to protect the retinal cells during vitreoretinal surgery.

SUMMARY OF THE INVENTION

The present invention is directed to the provision of an improved irrigating solution which is generally useful in the prevention or treatment of excitotoxicity, and is particularly useful in preventing or treating such damage associated with ophthalmic surgery. More specifically, the invention is directed to irrigating solutions comprising: one or more polyamine antagonists, electrolytes to maintain the stability of ophthalmic tissues, and a buffer.

DESCRIPTION OF PREFERRED EMBODIMENTS

Eliprodil and related polyamine antagonists of the present invention are a subset of EAA antagonists which bond to a unique location in the NMDA receptor. These compounds do not produce CNS side effects. Eliprodil and other polyamine antagonists are one of four classes of NMDA antagonists. (See, for example, Ornstein et al., "Antagonists of the NMDA receptor complex," *DN&P,* 7(1):5–12 (1994).) The classes include the competitive antagonists which antagonize the glutamate recognition site, non-competitive channel blockers; glycine antagonists and polyamine antagonists, the latter two modulate the glutamate response on the receptor. The glycine and polyamine modulatory sites are distinct. As aforementioned, antagonists of EAA receptors have been used in the CNS to prevent neuronal injury in animal models of ischemia, hypoglycemia, and trauma. Pharmacologically, competitive and non-competitive antagonists suffer from their inability to cross the blood-brain barrier and the fact that they can produce undesirable (psychotomimetic) side effects. Unlike other NMDA antagonists, the polyamine antagonists such as eliprodil partition across the blood-brain barrier and produce their actions at a modulatory site without side-effects typical of non-competitive antagonists. (See, for example, Lipton, S. A., "Prospects for clinically tolerated NMDA antagonists: open-channel blockers and alternative redox states of nitric oxide," *TINS,* 16(12): 527–532 (1993).)

Particularly preferred polyamine antagonists are certain 1-phenyl-2-piperidinoalkanol derivatives of formula (I), below:

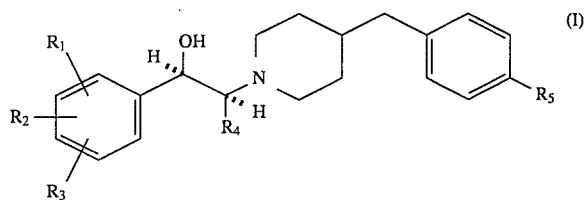

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

The compounds of formula (17) above are described in U.S. Pat. No. 4,690,931 (Wick et al.); however, there is no mention in that patent of ophthalmic indications for such compounds. Wick et al. also describe methods for synthesizing such compounds. The entire contents of U.S. Pat. No. 4,690,931 are incorporated herein by reference.

The most preferred compounds are: 2-[4-(4-fluorobenzyl)-piperidino]-1-(4-chlorophenyl)-ethanol, also known as eliprodil; 2-(4-benzylpiperidino)-1-(4-hydroxyphenyl)-propanol, also known as ifenprodil; or a pharmaceutically acceptable salts thereof. The structures of eliprodil and ifenprodil are shown below.

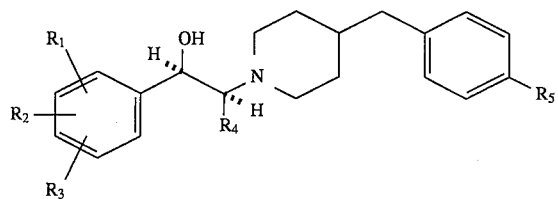

Eliprodil

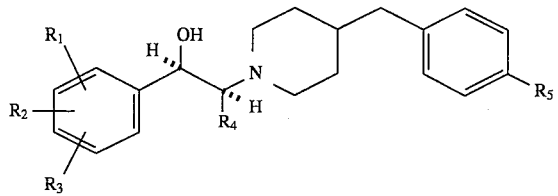

Ifenprodil

The irrigating solutions of the present invention will typically contain one or more polyamine antagonists at a concentration of about 1 picomolar (pM) to about 1 millimolar (mM), preferably 0.1 nanomolar (nM) to 100 micromolar (µM), most preferably 1nM-10 µM.

The solutions further comprise: electrolytes in an amount effective to maintain tissue stability and a buffer in an amount sufficient to maintain the pH of the composition in the range of 6.8 to 8.0.

The solutions can also include an energy source, such as dextrose, in an amount effective to satisfy the metabolic requirements of corneal endothelial cells and other ophthalmic tissues during the surgical procedure; an amount of bicarbonate effective to maintain the fluid pump system of corneal endothelial cells and other ophthalmic tissues. The irrigating solutions of the present invention can also include an amount of a free radical scavenger effective to protect the corneal endothelial cells and maintain normal function of those cells. The preferred free radical scavengers include ascorbate, glutathione, and cysteine, as well as esters, and analogues and other equivalents of these compounds. The most preferred free radical scavenger is glutathione. The solutions can contain one or more free radical scavengers in a concentration of from about 0.01 to about 3 mM/l.

The present invention may be embodied in various types of ophthalmic irrigating formulations, but will generally be provided in the form of an aqueous solution. As will be appreciated by those skilled in the art, some of the components of the formulations may need to be segregated prior to the time of use, due to considerations involving the chemical stability of certain components, the potential for adverse chemical interactions between certain components, and the methods of sterilization suitable for certain components.

The most preferred embodiment of the present invention is a two-part product similar to BSS Plus® Intraocular Irrigating Solution (Alcon Laboratories, Inc., Fort Worth, Tex.). The product is described in U.S. Pat. No. 4,550,022 which is incorporated herein by reference. The polyamine antagonist is added to either the neutral or acidic component of the two part BSS Plus® product depending on the polyamine antagonist's solubility and stability under either condition and its compatibility with the other ingredients. The compositions of the two parts are such that each is individually stable and may be separately stored for long periods. When mixed together the two parts form a tissue irrigating solution that may be used for surgery during the next 24 hours. The mixed solution is useful for ocular surgery as it contains the necessary factors to maintain endothelial cell integrity and corneal thickness during ocular surgery and protect retinal tissue. The combined irrigating solution contains the necessary ions for tissue stability, $Ca^{++}$, $Mg^{++}$, $Na^+$, $K^+$ and $Cl^-$ in a bicarbonate-phosphate buffer as well as reduced glutathione and dextrose. The electrolytes are provided in proportions conducive to maintaining the physical integrity and metabolism of corneal endothelial cells and other ocular tissues. For this purpose, the irrigating solution will typically contain from about 50 to about 500 mM $Na^+$, from about 1 to about 10 mM $K^+$, from about 0.1 to about 5 mM $Ca^{++}$, from about 0.1 to about 10 mM $Mg^{++}$ and from about 50 about 500 mM $Cl^-$. To maintain the osmotic stability of the cells, the osmolality is between about 260 and about 330 mOsm and preferably about 290–310 mOsm. So as to closely match the physiological pH of 7.4, the pH of the final irrigating solution is between about 6.8 and about 8.0 and preferably about 7.2–7.8. To maintain the fluid pump system, the bicarbonate concentration in the combined irrigating solution is between about 10 and about 50 mM. To stabilize the pH, an additional buffering agent is provided. Preferably the buffering agent is phosphate which is provided in sufficient quantity so that final phosphate concentration of the irrigating solution is between about 0.1 and about 5 mM. The final irrigating solution contains between about 1 and about 25 mM dextrose and between 0.01 and about 3 mM glutathione.

The neutral solution provides the phosphate and bicarbonate buffering moieties, preferably in the form of dibasic sodium phosphate and sodium bicarbonate. The pH of the solution is adjusted to about the physiological pH, of 7.4, preferably to between about 7.2 and about 7.8. As hereinbefore mentioned, the pH of a bicarbonate-containing solution is preferably above about 8.0 to prevent decomposition of the bicarbonate. It has been found, however, that the bicarbonate may be stabilized if it is added to a solution with a pH of above about 8 and thereafter adjusted to a pH between 7 and 8. Accordingly, when the neutral solution is prepared, $Na_2HPO_4$ is added prior to the addition of $NaHCO_3$, so that $NaHCO_3$ is dissolved in a solution with a pH of between about 8 and 9. The solution is thereafter adjusted with dilute acid, such as $H_2SO_4$, $H_3PO_4$ or HCl, to the desired final pH of the neutral solution. Alternatively, carbon dioxide may be added to adjust the pH.

Potassium and additional sodium are provided in the basic solution in the form of sodium and potassium salts, such as sodium or potassium chlorides, sulfates, acetates, citrates, lactates, and gluconates. The sodium and potassium are compatible with all of the moieties present in the finished tissue irrigating solution, and sodium chloride and potassium chloride may be added to either solution or divided between the solutions. However, in view of the fact that the neutral solution provides the buffer system, the pH of the final irrigation solution may be added to adjust the pH.

The acidic solution provides the $Ca^{++}$ in the form of calcium chloride, the $Mg^{++}$ in the form of magnesium chloride, the glutathione and the dextrose. The pH is adjusted to about 5 or less to provide long-term stability to the dextrose and glutathione.

Because of the requirement that the acidic solution have a low pH, it is preferable that the volume of the neutral solution greatly exceed the volume of the acidic solution and that the acidic solution contain no buffering agents. The acidic solution may be adjusted below a pH of about 5 with a relatively small amount of HCl. Because the acidic solution is unbuffered, its pH is a reflection of the acid concentration and less acid is needed to adjust the pH of a small volume. The large volume of buffered neutral solution may be adjusted very close to the final pH of the irrigating solution and will be relatively unaffected by the addition of the small volume of the acidic solution. Preferably, the ratio of the neutral solution volume to the acidic solution volume is about 10 to 1 to about 40 to 1.

The neutral solution and the acidic solution are sterilized and separately bottled or contained under sterile conditions by standard techniques, such as autoclaving, or use of sterilizing filters, but preferably by heat sterilization. Typically, the neutral solution, which preferably contains only inorganic moieties, is autoclaved, whereas the acidic solution, which preferably contains the organic components, is microfiltered. To avoid the need for measuring volumes in the hospital which may introduce possible error and/or contamination, it is highly preferred that particular volumes of the neutral and acidic solutions be bottled so that adding the entire content of a container of the acidic solution to the entire content of a container of the neutral solution results in the correctly formulated tissue irrigating solution. The solutions may be mixed up to 24 hours before a surgical procedure without the occurrence of significant pH change and without the formation of detectable precipitates and without degradation.

Precautions to maintain sterility of the solutions and to insure correct mixing of the acidic and neutral solutions cannot be overdone. While the manufacturer may take all due precautions to maintain quality control, carelessness by a technician may render all such precautions for naught. Any opening of a container, no matter how carefully performed, increases the likelihood of contamination in the contents. As one method of substantially eliminating the possibility of improper mixing and to reduce the likelihood of contamination, the solutions may be shipped in a container having a first chamber for the neutral solution, an isolated second chamber for the acidic solution and means to communicate the chambers without opening the container. Various types of containers for the shipment of multi-part medical solutions may be utilized. As one example, a container may have a lower chamber containing a measured volume of the neutral is solution separated by a membrane from an upper chamber containing a measured volume of the acidic solution or a lyophilized powder formed from that solution. The container cap may include a plunger means which, when depressed, causes a sharp point of blade depending therefrom to break the membrane. The container is thereafter agitated, as by shaking, to complete the sterile mixing in proper volume of the acidic and neutral solutions.

The proper mixing of the acidic and neutral solutions may also be carried out by aseptically removing the acidic solution from its package with a sterile syringe and needle and aseptically adding the acidic solution to the contents of the neutral solution package through the rubber stopper. Alternately, a sterile double-ended needle can be used to transfer the acidic solution to the neutral solution by aseptically inserting one end of the needle into the vial containing the acidic solution and then aseptically inserting the other end of the needle into the neutral solution package, whereby the vacuum that is maintained therein transfers the acidic solution to the neutral solution and is mixed. A two compartment syringe can also be utilized, with the lyophilized powder of the acidic solution in one compartment, and a diluent for the powder in the second compartment. The compartments are separated by a movable stopper or membrane which can be displaced by depressing the plunger of the syringe, thereby allowing the diluent to be combined with the powder. Once the powder is dissolved, the resulting solution is then added to the bottle containing the neutral buffered solution by inserting a cannula attached to the front of the syringe through a stopper in the top of the bottle.

The two-part solution of the present invention also provides an advantage as to safety if a technician should fail to properly mix the two solutions. The larger volume neutral solution is physiologic so that there is less chance of toxicity if the basic solution were used without the acidic solution being mixed therewith.

The present invention may be embodied in various types of formulations. The preferred formulation is described in the following example.

EXAMPLE 1

The following two-part formulation is similar to the BSS Plus® Intraocular Irrigating Solution available from Alcon Laboratories, Inc., Fort Worth, Tex., U.S.A. That product, which is described in U.S. Pat. No. 4,550,022 (Garabedian, et al.), consists of two solutions referred to as "Part I" and "Part II", respectively. The following description illustrates how that product or similar products could be modified to incorporate the present invention.

Part I (neutral solution) is made by dissolving sodium chloride, potassium chloride, and anhydrous dibasic sodium phosphate in water for injection at about 20° C. Then sodium bicarbonate is added and dissolved. Additional water for injection is added to make the desired volume and 1N HCl is added to adjust the pH to about 7.4. The solution is then passed through a 0.45 micron Millipore filter and placed in a bottle. The filled bottle is then stoppered, vacuumed and sealed. The sealed bottle is sterilized by autoclaving at 121° C. for about 23 minutes.

Part II (acidic solution) is made by dissolving calcium chloride dihydrate, magnesium chloride hexahydrate, dextrose, eliprodil, and glutathione in water for injection. The solution is then sterile filtered through a 0.22 micron membrane filter and aseptically filled into a presterilized bottle and sealed with a presterilized rubber stopper.

For many free radicals that are sensitive to oxygen, the container is flushed with nitrogen gas. Also, a nitrogen blanket is maintained over the solution the displace air and protect the solution from oxidation. Immediately after flushing the filled container with nitrogen gas, it is sealed by means of a presterilized rubber stopper.

When Parts I and II are combined, the composition of the resulting formulation is as follows:

| Ingredients | Concentration (mM) |
| --- | --- |
| Reduced Glutathione | 0.01–3.0 |
| Eliprodil | $10^{-6}$–$10^{-2}$ |
| Bicarbonate | 1–50 |
| Calcium | 0.1–5 |
| Magnesium | 0.1–10 |
| Potassium | 1–10 |
| Sodium | 50–500 |
| Phosphate | 0.1–5 |
| Glucose | 1–25 |
| Chloride | 50–500 |
| Sodium Hydroxide and/or | Adjust pH |
| Hydrochloric Acid | Adjust pH |
| Water for Injection | q.s. |

We claim:
1. An improved method of irrigating ophthalmic tissue during surgical procedures which comprises applying to the affected ocular tissue an irrigating solution comprising:

a pharmaceutically effective amount of a polyamine antagonist;

electrolytes in an amount effective to maintain tissue stability; and a buffer in an amount sufficient to maintain the pH of the composition in the range of 6.8 to 8.0.

2. The method of claim 1, wherein the polyamine antagonist is:

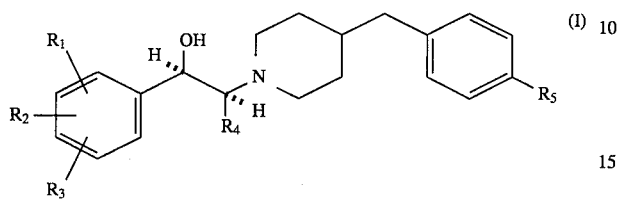

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

3. The method of claim 2, wherein the polyamine antagonist is Eliprodil.

4. An improved method of irrigating ophthalmic tissue during surgical procedures which comprises applying to affected ocular tissue an irrigating solution comprising a first part and a second part, said first part comprising a neutral solution containing bicarbonate and a buffer, and said second part comprising an acidic solution containing a free radical scavenger, an energy source, a polyamine antagonist, and divalent electrolytes, and monovalent electrolytes are contained in either said first part or said second part.

5. The method of claim 4, wherein the polyamine antagonist is:

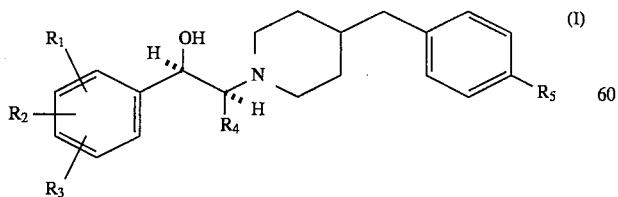

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)-erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical, and pharmaceutically acceptable acid addition salts thereof.

6. The method of claim 5, wherein the polyamine antagonist is Eliprodil.

7. The method of claim 4, wherein the irrigating solution comprises:

0.1 to 5 mM of the free radical scavenger;

1 to 25 mM of dextrose;

1 pM–1mM of a polyamine antagonist;

50 to 500 mM $Na^+$;

1 to 10 mM $K^+$;

0.1 to 5 mM $Ca^+$;

50 to 500 mM $Cl^-$;

10 to 50 mM bicarbonate; and 0.1 to 5 mM phosphate.

8. The method of claim 7, wherein the polyamine antagonist is:

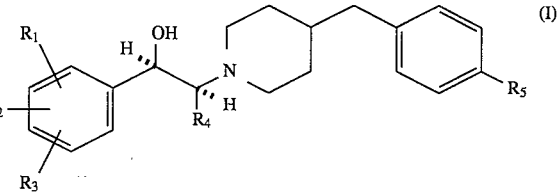

wherein:

$R_1$ represents a hydrogen atom, a halogen atom, a trifluoromethyl group, an alkyl group having from 1 to 4 carbon atoms, a hydroxyl group, an alkoxy group having from 1 to 4 carbon atoms, a benzyloxy group, an alkanoyloxy group having from 1 to 16 carbon atoms or a benzoyloxy group, or, when $R_2$ represents a hydroxyl or methoxy group in the 4-position and $R_3$ represents a hydrogen atom, $R_1$ may also represent a hydroxymethyl group, a carbamoyl group or an alkoxycarbonyl group having from 1 to 4 carbon atoms in the alkoxy part, $R_2$ represents a hydrogen atom, a halogen atom, an alkyl group having from 1 to 4 carbon atoms, a hydroxyl group or an alkoxy group having from 1 to 4 carbon atoms, $R_3$ represents a hydrogen atom or an alkyl group having from 1 to 4 carbon atoms, $R_4$ represents an alkyl group having from 1 to 4 carbon atoms, in which case the compounds are in the (±)- erythro form, or, when $R_3$ represents a hydrogen atom, $R_4$ may also represent a hydrogen atom, and $R_5$ represents a hydrogen atom, a halogen atom, an alkyl group having from 1 to 4 carbon atoms, an alkoxy group having from 1 to 4 carbon atoms or a set of three methoxy groups in the 3-, 4- and 5-positions of the benzyl radical,
and pharmaceutically acceptable acid addition salts thereof.

9. The method of claim 6, wherein the polyamine antagonist is Eliprodil.

10. The method of claim 7, wherein the free radical scavenger is selected from the group consisting of ascorbate, glutathione, and cysteine.

* * * * *